United States Patent [19]

Vumbaca

[11] Patent Number: 5,277,312
[45] Date of Patent: Jan. 11, 1994

[54] SYRINGE STORAGE AND DISPOSAL CONTAINER

[75] Inventor: Gino A. Vumbaca, Frenchs Forest, Australia

[73] Assignee: Health Administration Corporation, North Sydney, Australia

[21] Appl. No.: 847,103

[22] PCT Filed: Oct. 25, 1990

[86] PCT No.: PCT/AU90/00510

§ 371 Date: Jun. 1, 1992

§ 102(e) Date: Jun. 1, 1992

[87] PCT Pub. No.: WO91/06328

PCT Pub. Date: May 16, 1991

[30] Foreign Application Priority Data

Oct. 27, 1989 [AU] Australia ............................ PJ7073
Oct. 27, 1989 [AU] Australia ............................ PJ7074
Jun. 15, 1990 [AU] Australia ............................ PK0663

[51] Int. Cl.$^5$ ................................... B65D 83/10
[52] U.S. Cl. ................................... 206/366; 206/365; 206/370; 220/523; 220/531
[58] Field of Search ............... 206/363, 364, 365, 370, 206/366, 563, 564; 220/4.23, 507, 523, 553, 531, 555, 908

[56] References Cited

U.S. PATENT DOCUMENTS

| | | | |
|---|---|---|---|
| 1,625,035 | 4/1927 | Lilly | 206/365 |
| 2,492,326 | 12/1949 | Scotti | 206/364 |
| 2,720,969 | 10/1955 | Kendall | 206/365 |
| 4,332,323 | 6/1982 | Reenstierna | 206/365 |
| 4,520,926 | 6/1985 | Nelson | 206/366 |
| 4,600,112 | 7/1986 | Shilington et al. | 206/366 |
| 4,657,138 | 4/1987 | Watson | 206/366 |
| 4,658,957 | 4/1987 | Gordon et al. | |
| 4,775,057 | 10/1988 | Zingeser | 206/366 |
| 4,850,484 | 7/1989 | Denman | 206/366 |
| 4,863,451 | 9/1989 | Marder | 206/366 |
| 4,875,583 | 10/1989 | Nosanchuk | 206/365 |
| 4,892,525 | 1/1990 | Hermann, Jr. et al. | 206/365 |
| 4,927,018 | 5/1990 | Yang et al. | 206/365 |
| 4,930,631 | 6/1990 | Bruno | 206/366 |
| 4,936,449 | 6/1990 | Conard et al. | 220/908 |
| 4,969,554 | 11/1990 | Sawaya | 206/366 |
| 4,973,315 | 11/1990 | Sincock | 206/365 |

*Primary Examiner*—David T. Fidei
*Attorney, Agent, or Firm*—Bernard L. Kleinke; Jerry R. Potts

[57] ABSTRACT

A syringe container (10) which holds both sterile and soiled syringes. The sterile and soiled syringes are separated by a dividing plate (19) which is hinged to a frame (16). The frame (16) defines a rectangular aperture (17) over an open end (17) of the container (10). The soiled syringes are pushed through the aperture (17) into a retaining area (21). The aperture (17) is provided with two lugs (18) which prevent the soiled syringes from being removed from the retaining area (21). The sterile syringes are contained in an area (22) which is accessible through open end (12). The container (10) is provided with a hinged lid (13) which snap fits over the open end (12).

12 Claims, 3 Drawing Sheets

SYRINGE STORAGE AND DISPOSAL CONTAINER

The present invention relates to a syringe container for retaining soiled syringes such that syringes retained within the container cannot be removed from the container without the application of excessive force to or destruction of the container.

BACKGROUND OF THE INVENTION

The devastating effect upon the population at large caused by the HIV virus is widely acknowledged and various attempts ranging from education to incarceration of carriers have been made to stem the spread of the virus. Contact with contaminated blood is an acknowledged vehicle for transfer of the virus and one specific form of such transfer is the sharing of syringes by intravenous drug users. The present invention seeks to reduce the likelihood of the transfer of the HIV virus by providing a tamper-proof container for soiled syringes thereby reducing the number of soiled syringes that are inappropriately disposed of in the community and to encourage intravenous drug users not to share syringes. Although the invention is described in this context it is to be understood to have wider application and is in fact appropriate for retaining any soiled syringe.

In recognition of the above, the applicant has developed the present invention and it is envisaged that containers filled with sterile syringes will be made available free of charge or for a nominal charge to intravenous drug users through pharmacies or the like. It is then intended that the drug user will use a sterile syringe from the container for each injection and after use return the soiled syringe to be retained within the tamper-proof container. When all sterile syringes have been used and returned to the container, the container is returned to a pharmacy or the like and effectively swapped for a further container containing sterile syringes. Arrangements are then to be put in place for the safe disposal of the containers containing the soiled syringes. Typically this would involve collection of returned containers and their incineration along with other commonly incinerated medical refuse.

It can therefore be seen that if used in the manner envisaged, the present invention should reduce the spread of the HIV virus by reducing the chance of members of the public accidentally contacting a soiled syringe which has been inappropriately disposed of in a public area and should encourage intravenous drug users not to share needles.

Preferred embodiments of the present invention are presently being used in the Australian state of New South Wales and are referred to as "Fitpacks". The use of Fitpacks in other Australian states is planned for the near future.

Prior to the advent of the present invention, the New South Wales State Government had established thirty Needle and Syringe Exchange Programmes (NSEPs) which between them operated from approximately eighty outlets. These outlets varied from a dedicated fixed location such as one service offered by a sexually transmitted diseases clinic to outreach services including needle and syringe distribution from vehicles in public areas.

In addition to the established NSEPs, arrangements have been made with the Pharmacy Guild of Australia to distribute and exchange Fitpacks. There are presently over 400 pharmacies throughout New South Wales dispensing Fitpacks. The Fitpacks are dispensed and exchanged free of charge from NSEPs and exchanged free of charge on an old for new exchange basis from pharmacies. In the absence of a used Fitpack for exchange, new Fitpacks can be purchased from pharmacies for A$3.00. The New South Wales State Government therefore bears the brunt of the costs associated with the programme but this is viewed as being desirable when the object of the programme is taken into consideration.

NSEPs order empty Fitpacks directly from the manufacturer whilst arrangements have been made for the pharmacies to obtain empty Fitpacks from their regular wholesalers. Needles and syringes are obtained independently and the empty Fitpacks are filled with needles and syringes at the various points of distribution by NSEP workers and pharmacists.

Individual arrangements have been made with each NSEP and pharmacy for the safe disposal of used Fitpacks under established clinical waste guidelines. The disposal involves incineration above 1100° C. and it is noted that the preferred embodiments of the invention presently used are manufactured from polypropylene which does not create environmental hazards upon incineration.

No quantitative data is available to date for the return rate of used Fitpacks but the qualitative observation has been that the rate of return has exceeded 65% which was the figure prior to the introduction of the Fitpack programme.

SUMMARY OF THE INVENTION

It is an object of the present invention to provide a syringe container for retaining soiled syringes such that syringes retained within the container cannot be removed from the container without the application of excessive force to or destruction of the container and accordingly, the present invention provides a syringe container comprising an open ended substantially hollow shell housing retaining means arranged to retain soiled syringes and containing means arranged to contain sterile syringes, whereby retained soiled syringes cannot be removed from the container without the application of excessive force to or destruction of the container and contained sterile syringes are readily removed from the container.

Preferably, the container includes a lid which can be closed to hide retained and contained syringes from view leaving the container with a neat external appearance.

The retaining means of the container preferably incorporates an aperture which is accessible from the open end of the shell and into which extend one or more resiliently deformable lugs which are arranged to facilitate one-way passage of a syringe into the container.

In a first embodiment of the invention the lugs of the aperture are biased to a position which substantially closes the aperture. The lugs however deform sufficiently to allow a syringe to pass completely through the aperture and after passage return to a position in which the retained syringe cannot return through the aperture to be removed from the container.

The retaining means preferably further incorporates a dividing plate which extends from the open end of the shell to effectively divide the container into two portions; one in which soiled syringes are retained and the other in which sterile syringes are contained. The soiled syringe retaining area is accessible through the aperture and with this arrangement it can readily be seen how the invention can be used in the manner envisaged by the applicant. More preferably, the dividing plate can be moved within the container to vary the size of each of the compartments. This enables maximisation of the use of the total area of the container by increasing the size of the soiled syringe retaining area when further room is required while correspondingly reducing the size of the sterile syringe containing area after removing a sterile syringe from the container. This feature can be achieved in a number of ways, for example, by mounting the dividing plate on a track which can be manually moved to increase the size of the soiled syringe retaining area after removal of a sterile syringe. Preferably however, the dividing plate is mounted on a hinge adjacent to the open end of the container and is biased to move in the direction which maximises the size of the soiled syringe retaining area. Accordingly, the size of the soiled syringe retaining area will progressively be increased simply by removal of sterile syringes from the container.

In a second embodiment of the invention, the aperture is located at the entrance to a pocket having two substantially parallel walls extending away from the open end of the shell. Two said lugs are provided extending inwardly from the walls of the pocket and the lugs are at the same level in the pocket. The lugs are resiliently deformable and biased to positions in which they are separated by a distance which is sufficient to permit passage of the body of a syringe. The body of a syringe is to be understood to be the barrel which houses the plunger, the needle and moulding which attaches it to the barrel and the cap which fits over the needle if fitted. The distance between the lugs is however insufficient to permit passage of the flange of a syringe which is to be understood to be that part of a syringe upon which the index finger and third digit generally rest when force is applied to the plunger by the thumb. Upon application of sufficient force, the lugs deform to permit passage of the flange and then return to their original position.

The pocket preferably further comprises guide means arranged to maintain the body of the syringe substantially parallel with the walls of the pocket during passage of the syringe between the two lugs. More preferably, the guide means comprise integrally moulded protrusions which extend from walls of the pocket below the two lugs with the protrusions being separated by a distance sufficient to permit passage of the body of the syringe but insufficient to permit passage of the flange of the syringe.

Preferably, the lugs are sufficiently remote from the open end of the shell to allow a sterile syringe to be completely within the container when the flange of the sterile syringe rests on the lugs. Accordingly, a sterile syringe can rest upon the lugs, be removed from the container and used, and subsequently returned to the container to be retained following pushing the flange of the syringe beyond the lugs. In this embodiment, each pocket is therefore designed to contain one sterile syringe and subsequently retain one soiled syringe. A container can therefore comprise a plurality of pockets to contain and subsequently retain a corresponding plurality of syringes.

In both embodiments of the invention, the shell and the retaining means are preferably separately moulded from plastics material and ultra-sonically welded together.

BRIEF DESCRIPTION OF THE DRAWINGS

Notwithstanding any other forms that may fall within its scope, two preferred embodiments of the invention will now be described, by way of example only, with reference to the accompanying drawings, in which.

BEST MODE OF CARRYING OUT THE INVENTION

Figure 1:
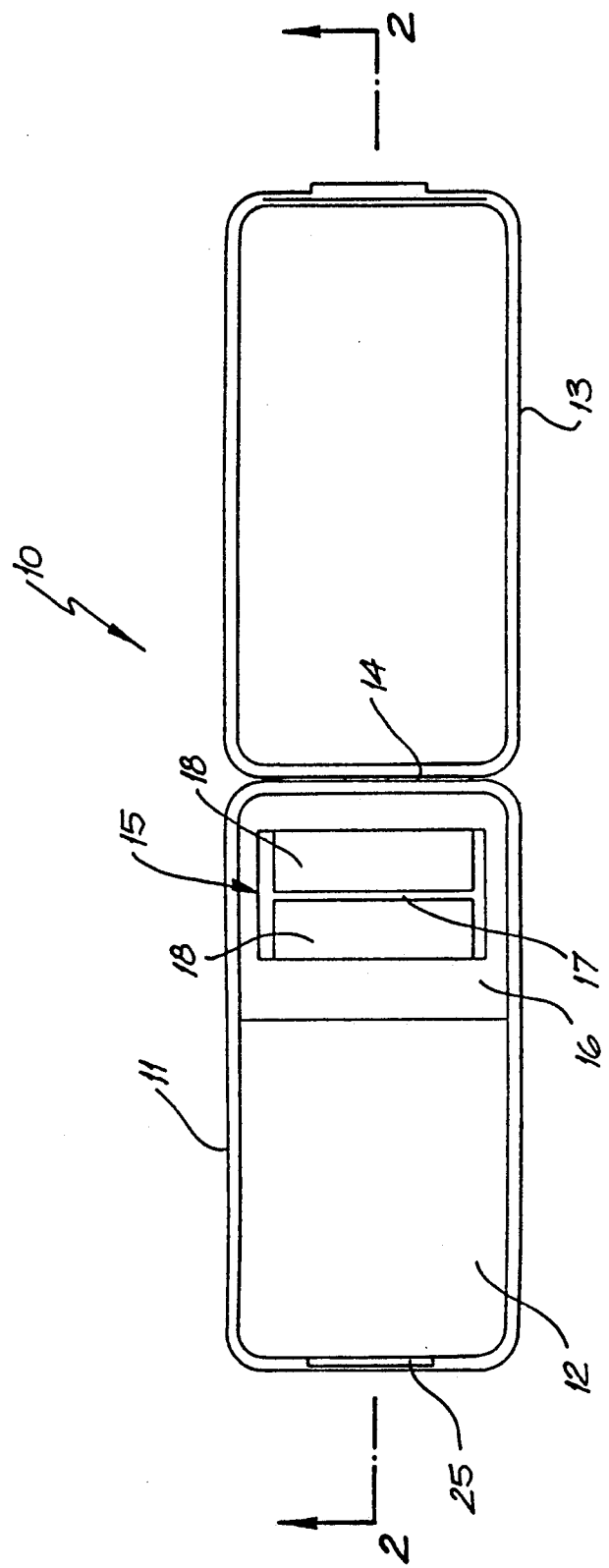
FIG. 1 is a plan view of a first embodiment of the present invention showing the lid of the container in the fully opened position.
Figure 2:
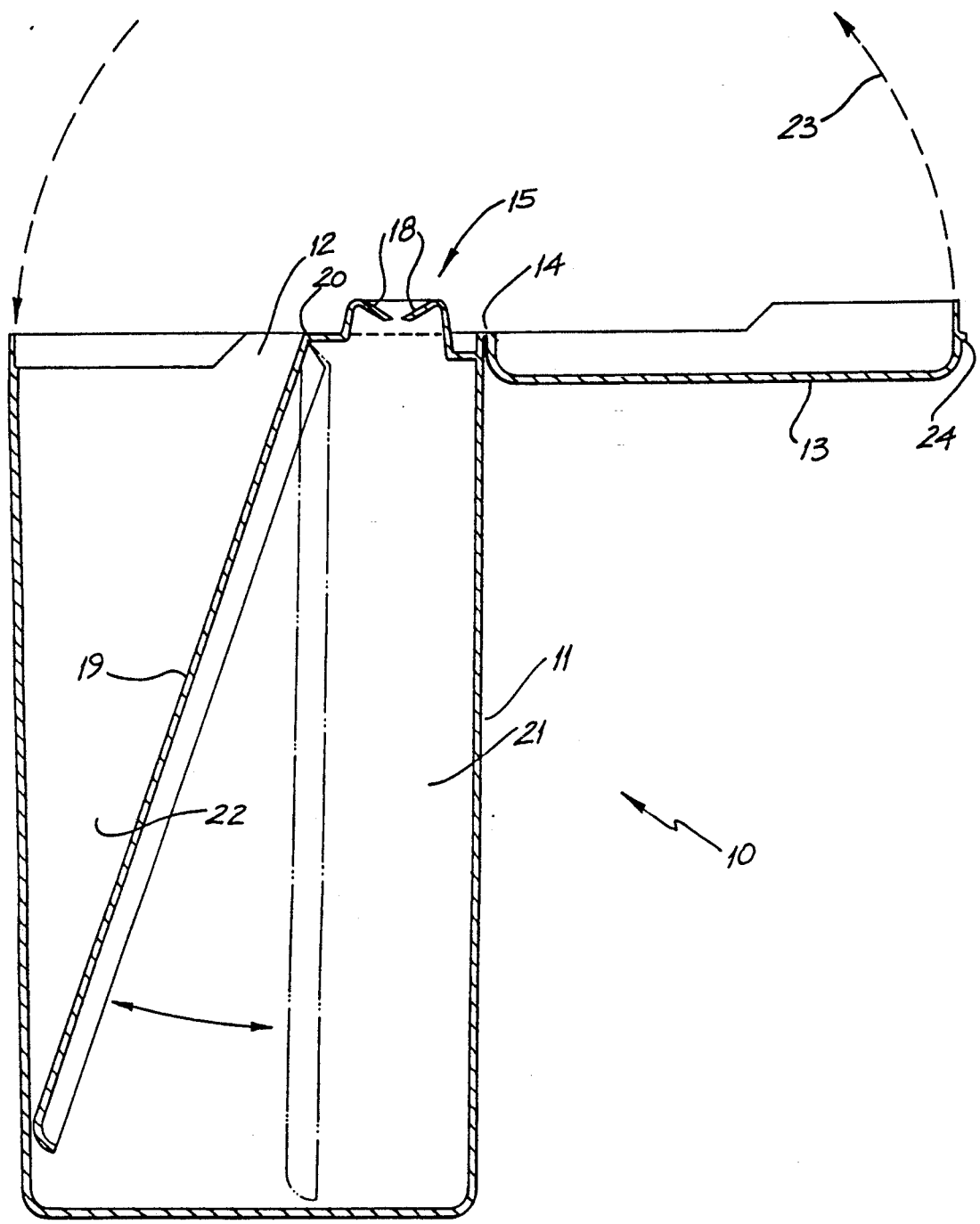
FIG. 2 is a sectional elevational view through section line 2—2 of FIG. 1.

As illustrated in FIG. 1, a container 10 is provided comprising a substantially hollow shell 11 having an open end 12, a lid 13 which is mounted to the shell 11 by hinge 14 and retaining means 15 arranged to retain soiled syringes in the container.

The retaining means 15 is in the form of a frame 16 defining a rectangular aperture 17 which is substantially closed by two resiliently deformable rectangular lugs 18 extending into the aperture. Alternatively, the aperture could be of any desired shape and could for example be circular in which case there would be a number of substantially triangularly shaped lugs which substantially close the aperture. A dividing plate 19 is mounted to the frame by hinge 20 and is biased to the position illustrated by the full lines. The dividing plate 19 divides the body of the container into a soiled syringe retaining area 21 and a sterile syringe containing area 22.

In use, sterile syringes in their plastic wrapping are packed into area 22 and in so doing move dividing plate 19 to the position illustrated by the dashed lines. Sterile syringes are then removed from area 22, used and subsequently returned to the container by passing them through aperture 17 between lugs 18. Following passage through the aperture 17, a soiled syringe is retained in area 21 and as this process is repeated the dividing plate 19 progressively moves from right to left until eventually it adopts the position shown in the full lines with area 22 empty and area 21 full.

The container 10 can be closed by moving lid 13 about hinge 14 in the direction of arrow 23 with lug 24 ultimately engaging with recess 25 to snap fit the container closed and hide the contents from view.

Figure 3:
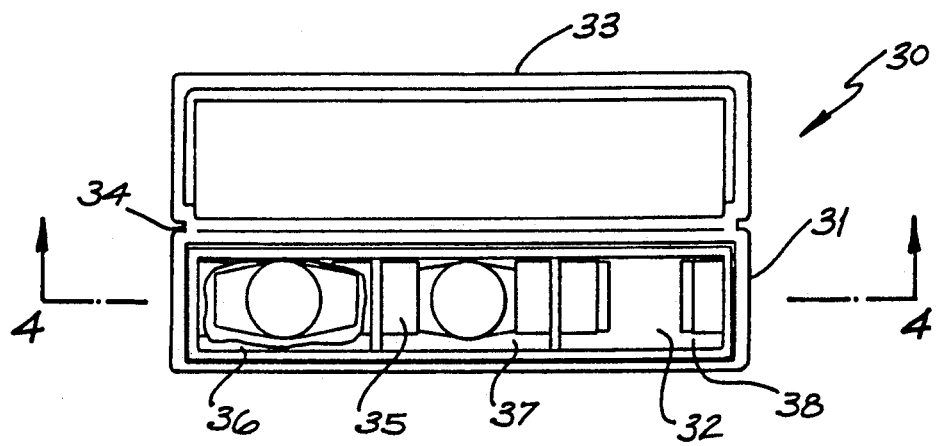
FIG. 3 is a plan view of a second embodiment of the invention showing the lid in the fully opened position.
Figure 4:
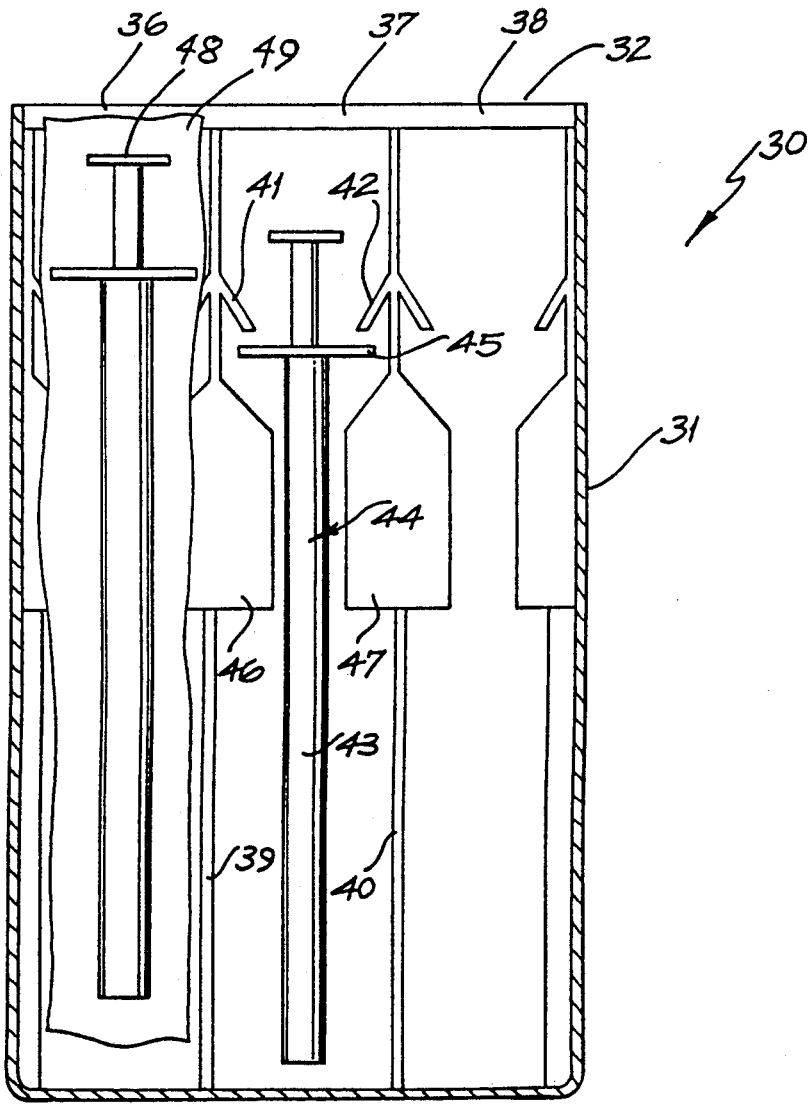
FIG. 4 is a sectional elevational view through section line 4—4 of FIG. 3.

In an alternative embodiment of the invention, as illustrated in FIG. 3, a container 30 is provided comprising a substantially hollow shell 31, having an open end 32, a lid 33 which is mounted to the shell 31, by hinge 34 and retaining means 35 arranged to retain soiled syringes in the container.

The retaining means 35 incorporate a number of apertures in the form of three similar pockets 36, 37 and 38. By way of example, pocket 37 has two parallel walls 39 and 40 which extend away from the open end 32 of the shell. Resiliently deformable lugs 41 and 42 extend from walls 39 and 40 respectively and are biased to positions in which the body 43 of syringe 44 can pass between them with passage of flange 45 being restricted. Guiding protrusions 46 and 47 extend from walls 39 and 40 respectively to keep the body 43 of the syringe substantially parallel with the walls when passing between lugs 41 and 42.

In use, sterile syringe 48 housed within plastic wrapping 49 is fully contained within the container sitting in pocket 36, the flange of syringe 48 inhibiting the syringe from passing the lugs of pocket 36. Syringe 48 is therefore readily removed from the container, unwrapped and used and subsequently returned to the pocket which for purposes of illustration is to be considered pocket 37. The soiled syringe is inserted into the pocket and its travel is guided by protrusions 46 and 47 until the flange rests upon lugs 41 and 42. At that point, force is exerted down upon the syringe which deforms lugs 41 and 42 allowing the flange of the syringe to pass and thus retaining the syringe in the pocket whereby the syringe cannot be removed from the container without the application of excessive force to or destruction of the container.

The container 30 can be closed by moving lid 33 about hinge 34 until the lid force fits into the shell to close the container and hide the contents from view.

I claim:

1. A syringe container for syringes each having a body including a radially outwardly projecting flange, comprising:
   openable shell housing having walls and having an access opening and being adapted for storing sterile syringes in a freely removable manner or soiled syringes in a captured manner to help prevent unwanted accidental needle punctures as well as reuse of the soiled syringes;
   closure means for being disposed over said opening to retain the sterile syringes within said housing and for being removed from the opening to permit access to the interior of the housing;
   a pair of resiliently deformable lugs each having a top surface for engaging the flange, said lugs being spaced by a distance sufficiently large to receive freely the syringe body and sufficiently small to be smaller than the width of the flange, said lugs depending angularly downwardly in a spaced apart manner for permitting a syringe body to be inserted freely between said lugs until the syringe flange engages the top surfaces of said lugs to force them away from one another to permit the full insertion of the syringe and thereafter capturing it in place by the lugs snapping back to their unstressed positions;
   common interior wall means extending axially within said shell housing for defining with the housing walls a soiled syringe receiving pocket means to receive and store a soiled syringe, and a sterile syringe receiving pocket means to receive and store a sterile syringe, to enable both a soiled syringe and a sterile syringe to be stored side by side within said housing without causing the sterile syringe from becoming contaminated by the soiled syringe.

2. A container as claimed in claim 1 wherein the shell housing is an open ended hollow cuboid, said closure means comprises a rectangular lid hingedly mounted to an edge of the access opening of the shell housing and the lid is arranged to be secured over the access opening in a closed relationship therewith.

3. A container as claimed in claim 1, wherein said soiled syringe receiving pocket means and said sterile syringe receiving pocket means include an access aperture.

4. A container as claimed in claim 3 wherein the aperture is rectangular and there are two rectangular lugs.

5. A container as claimed in any one of claims 3 or 4 wherein the aperture is located at substantially the access opening of the shell.

6. A container as claimed in claim 5 wherein said common interior wall means includes a dividing plate arranged to provide a barrier between a soiled syringe retaining area within said soiled syringe receiving pocket means, and a sterile syringe containing area within said sterile syringe receiving pocket means wherein the soiled syringe retaining area is only accessible to such a syringe through the aperture.

7. A container as claimed in claim 6 wherein the plate is movable from a first position in which the sterile syringe containing area is minimized and the soiled syringe retaining area is maximized to a second position in which the sterile syringe containing area is maximized and the soiled syringe retaining area is minimized.

8. A container as claimed in claim 7 wherein the aperture is defined by a frame, the plate is hingedly mounted to an edge of the frame and resiliently biased to the first position whereby the loading of sterile syringes into the containing area progressively moves the plate to the second position.

9. A container as claimed in claim 1 wherein said soiled syringe receiving pocket means and said sterile syringe receiving pocket means each further comprises guide means arranged to maintain the body of a syringe substantially parallel with the walls of the corresponding syringe receiving pocket means during passage of the syringe between the two lugs.

10. A container as claimed in claim 9 wherein the guide means comprise integrally molded protrusions which extend inwardly from the walls of said pocket means, the protrusions located remote from the access opening of the shell and separated by a distance sufficient to permit passage of the body of a syringe but insufficient to permit passage of the flange of the syringe.

11. A container as claimed in any one of claims 9 or 10 wherein the lugs are located sufficiently far from the access opening of the shell housing to allow the sterile syringe to be stored completely within the shell housing when the flange of the sterile syringe rests on the top surface of the lugs.

12. A container as claimed in claim 1 wherein the shell housing and the lugs are separately molded from plastics material and ultra-sonically welded together.

* * * * *

UNITED STATES PATENT AND TRADEMARK OFFICE
CERTIFICATE OF CORRECTION

PATENT NO. : 5,277,312
DATED : January 11, 1994
INVENTOR(S) : Gino A. Vumbaca

It is certified that error appears in the above-indentified patent and that said Letters Patent is hereby corrected as shown below:

On title page, item [56] "References Cited", after 4,658,957 4/1987" delete "Gordon et al.", and substitute therefor --Guth, et al.--.

Signed and Sealed this

Twenty-sixth Day of July, 1994

Attest:

BRUCE LEHMAN

*Attesting Officer*    *Commissioner of Patents and Trademarks*